United States Patent [19]

Zupancic et al.

[11] Patent Number: 4,664,757
[45] Date of Patent: * May 12, 1987

[54] METHOD AND APPARATUS FOR GAS DETECTION USING PROTON-CONDUCTING POLYMERS

[75] Inventors: Joseph J. Zupancic, Bensenville; Raymond J. Swedo, Mt. Prospect; Sandra L. Petty-Weeks, Naperville, all of Ill.

[73] Assignee: UOP Inc., Des Plaines, Ill.

[*] Notice: The portion of the term of this patent subsequent to May 12, 2004 has been disclaimed.

[21] Appl. No.: 814,345

[22] Filed: Dec. 27, 1985

[51] Int. Cl.[4] .............................................. G01N 27/58
[52] U.S. Cl. ..................................... 204/1 T; 204/421; 204/426; 204/427
[58] Field of Search ........................ 429/30, 33, 192; 204/129, 130, 252, 277, 278, 1 T, 1 B, 1 F, 1 S, 421, 424, 425, 426, 427

[56] References Cited

U.S. PATENT DOCUMENTS

| Re. 28,792 | 4/1976 | Ruka et al. ....................... 204/427 X |
| 3,265,536 | 8/1966 | Miller et al. ..................... 204/296 X |
| 3,342,558 | 9/1967 | Reinecke ........................... 204/421 X |
| 3,392,096 | 7/1968 | Lawton et al. .................. 204/159.15 |
| 3,489,670 | 1/1970 | Maget ................................. 204/129 |
| 3,576,730 | 4/1971 | Spacil ................................ 204/427 X |
| 4,179,491 | 12/1979 | Howe et al. ........................ 423/253 |
| 4,295,952 | 10/1981 | de Nora et al. ..................... 204/252 |

*Primary Examiner*—John F. Niebling
*Assistant Examiner*—Nam X. Nguyen
*Attorney, Agent, or Firm*—Thomas K. McBride; John F. Spears, Jr.; Richard J. Cordovano

[57] ABSTRACT

Apparatus and method for detecting and measuring hydrogen and gaseous compounds capable of dissociating into or combining with hydrogen ions using a solid electrolyte concentration cell. A novel proton-conducting membrane comprised of an interpenetrating polymer network serves as the solid electrolyte. A reference gas or a solid reference substance is used. For increased strength, a membrane may be composited with or utilized with a porous support.

21 Claims, 5 Drawing Figures

METHOD AND APPARATUS FOR GAS DETECTION USING PROTON-CONDUCTING POLYMERS

FIELD OF THE INVENTION

This invention relates to electrochemical measurement and detection. More specifically, it relates to the use of a novel water-insoluble solid electrolyte and a catalyst in detecting certain gases. The solid electrolyte is an interpenetrating polymer network.

BRIEF SUMMARY OF THE INVENTION

The present invention provides methods and apparatus for detecting gaseous hydrogen, hydrogen ion, dissociable hydrogen compounds, and compounds capable of combining with hydrogen ion, in order to indicate the presence or absence of these substances and, where desired, provide quantitative information on the amount present.

A novel solid electrolyte is used in the present invention. We have discovered that a water-insoluble membrane may be obtained by admixing sulfuric acid or a phosphoric acid with an organic polymer which is at least partially compatible with said acid to form a host polymer blend which, in combination with a guest polymer, forms an interpenetrating polymer network which is useful in gas detection. This membrane is capable of acting as a proton conductor in a hydrogen detector where molecular hydrogen is converted into protons on one side of the membrane, protons are then transported through the membrane, and protons are recombined with electrons to form molecular hydrogen on the other side. The membrane is also useful in detection of gases capable of dissociating into or combining with hydrogen ions.

In addition, the composition of matter utilized for said membrane may be composited on a flexible porous support to form a composite membrane which possesses increased strength as well as being a protonic conductor or it may be used with a rigid porous support. Examples of material used for such porous support include glass cloth, polysulfone, and ceramics. Even without a support, a membrane of the present invention is stronger than prior art membranes.

The invention utilizes a concentration cell whose electrolyte is said membrane or composite membrane. A membrane is mounted in a sample cell or membrane housing having a sample gas chamber and a reference chamber, which chambers are separated by a partition comprising the membrane. The sample gas chamber contains the gas sample of interest, which must include a component capable of dissociating to form hydrogen ions or capable of combining with hydrogen ions. In the other chamber is a reference gas whose composition is known or a solid reference substance which exhibits a substantially constant known hydrogen partial pressure during use of the invention. Molecular transport through the membrane must be sufficiently slow so that gases will not mix by diffusing through it.

A catalytic agent for promotion of dissociation or combination is in intimate contact with the membrane on the sample gas side. Catalytic agent is also provided in a like manner on the reference side. It is not necessary that the same catalyst agent be used on both sides. Means for forming electrical contact and transferring electrons to and from an external circuit are provided on each side of the electrolyte in intimate contact with catalytic agent. The cell EMF is measured across said means for forming electrical contact and provides an indication of the presence of hydrogen or gases capable of combining with it in the sample gas and/or a quantitative measure of the amount of such which is present.

The method of the invention may be summarized as a method for detection, in a gas sample, of a gaseous component which is capable, in the presence of a catalytic agent, of dissociating to yield hydrogen ions or of combining with hydrogen ions, such method comprising contacting said gas sample with a first surface of an interpenetrating polymer network membrane and detecting EMF between means for forming electrical connection with two separate portions of a catalytic agent effective to promote dissociation and combination, where a first portion of catalytic agent is in contact with said first surface and a second portion of catalytic agent is in contact with a second surface of said membrane, which membrane isolates said gas sample from a reference substance and has said second surface exposed to the reference substance, said membrane comprising a host polymer blend and a guest polymer, where the host polymer blend is comprised of an acid selected from a group consisting of phosphoric acids and sulfuric acid and a polymer selected from a group of polymers or copolymers having repeat units selected from a group comprising hydroxyethylene, ethyleneimine, acrylic acid, ethylene oxide, 2-ethyl-2-oxazoline, polyphenolic structures such as phenol formaldehyde resins, acrylamide, N-substituted acrylamides, 4-vinylpyridine, methacrylic acid, N-vinylimidazole, vinyl sulfonic acid, and 2-vinylpyridine, and the guest polymer is formed from a monofunctional monomer selected from a group consisting of acrylic acid, methacrylic acid, acrylamide, methacrylamide, 2-acrylamido-2-methylpropanesulfonic acid, N-benzylacrylamide, N-ethylmethacrylamide, N-phenylacrylamide and N-phenylmethacrylamide, and a difunctional cross-linking agent selected from a group consisting of methylenebisacrylamide, N,N-diallylacrylamide, m-xylenebisacrylamide, and N,N'-trimethylenebisacrylamide.

A calculating device may be used to automatically calculate concentrations, or calculation may be accomplished manually. This device may receive input from a temperature probe, or temperature may be entered manually for use in the calculation. Temperature of the gas or gases and/or the membrane housing may be controlled at a pre-established value. The catalytic agent may be platinum, palladium, or alloys thereof. The catalytic agent may be electrically conductive. Where temperature of the sample gas is too high or low for effective detection, it may be adjusted before the gas is contacted with the electrolyte element. It may be necessary to adjust the concentration, in a known manner, of sample gas contacting the membrane in order to achieve effective detection.

BACKGROUND OF THE INVENTION

The present invention utilizes a solid electrolyte sensor for detection of certain gases. The Nernst equation describes the behavior of sensing devices using solid electrolytes. When two media with different partial pressures, $P_1$ and $P_2$, of a particular substance present in both media are separated by a solid electrolyte (ionic conductor) and conducting electrodes are attached to both sides of the ionic conductor, an EMF is generated which is related to the partial pressure as follows:

$$EMF = E_o + \frac{RT}{nF} \ln \frac{P_2}{P_1},$$

where R is the gas constant, T is absolute temperature, F is the Faraday constant, $E_o$ is the standard oxidation-reduction potential difference, EMF is electromotive force, and n is the number of electrons per molecule of product from the overall cell reaction.

If the system described by the above equation behaves nonideally, the partial pressures must be replaced by fugacities. Another factor which may need to be considered in regard to a particular system is the rate of dissociation to form the ions which pass through the solid electrolyte. This may be a limiting factor to the transfer of ions through the electrolyte. The monofunctional monomer which is employed to form the guest polymer differs from any of the monomeric repeat units which comprise the organic polymer in the host polymer blend so that an interpenetrating polymer network may be formed. The rate of dissociation can be calculated by means of the equilibrium constant for the dissociation reaction.

The magnitude of EMF produced is generally in accordance with the parameters discussed herein: the Nernst equation and, where applicable, the dissociation equilibrium constant. However, required practice in measuring concentration is to periodically calibrate the measuring apparatus by use of samples whose composition is known. Thus, exact adherence to theoretical relationships is not required of commercially used methods and apparatus. The primary commercial requirement is repeatability.

In a majority of cases, the admixture of an organic compound, especially in a polymeric state, with an inorganic compound, results in a phase separation, due to the fact that the two systems are immiscible in nature. However, in a macroscopically homogeneous polymer blend, which we term a host polymer blend, may be prepared by admixing organic and inorganic components as discussed herein; the resulting substance (the host polymer blend) is not merely a physical mixture but exhibits a degree of interaction, that is, some amount of chemical interaction exists. The host polymer blend is then admixed with a monomer and a difunctional cross-linking agent in a compatible solvent. The mixture is cast on a smooth surface and the solvent removed to form a membrane. The monomer is polymerized to form a polymer termed the guest polymer, thereby forming an interpenetrating polymer network membrane.

Interpenetrating polymer networks are known to those skilled in the art. There are three general classes of interpenetrating polymer networks: sequential, simultaneous, and latex. The classes differ in method of preparation. In order to prepare an interpenetrating polymer network of the sequential class, a first polymer, termed a host polymer, is prepared in the absence of a second monomer. The host polymer is then mixed with a second monomer and a cross-linking agent in a compatible solvent. After removal of the solvent, the second monomer and cross-linking agent are polymerized to yield the guest polymer of the interpenetrating polymer network and the guest polymer is cross-linked to itself. An interpenetrating polymer network is more than a blend of two polymers. It is a new polymer system having properties which are a combination of those possessed by the host polymer and the guest polymer. However, there is no chemical bonding between the host and guest polymers. In the new polymer system, the host and guest polymer chains are permanently entangled, or intertwined, with one another. It is impossible to separate the two polymers by chemical methods (such as leaching or dissolving one polymer away from the other). It can be seen that the present invention may be termed an interpenetrating polymer network.

Substances which are permeable by gases in a selective manner are known and utilized in a variety of applications. A membrane formed in accordance with the present disclosure is substantially impermeable to ions and gases, including hydrogen gas, but does not allow hydrogen ions to pass through it. For background information relating to the principles of the present invention, reference may be made to the book *Solid Electrolytes and Their Applications*, edited by Subbarao, Plenum Press, 1980.

Low mechanical strength has been a common problem when attempting to apply permselective membranes. The present invention provides a membrane whose mechanical strength is increased by compositing it with other materials, but whose desirable properties are not lost as a result of doing so.

Also used in the present invention is a solid substance which is a substitute for a reference gas, which reference gas is one of the two media mentioned above in the discussion of the Nernst equation. It is highly desirable to use a solid reference substance, which requires only periodic replacement, instead of maintaining a continuous reference gas flow, or in appropriate situations, maintaining a sealed chamber of reference gas. The reference substance is in intimate contact with the catalytic agent on the reference side of the membrane. One substance may serve as both reference substance and catalytic agent.

DETAILED DESCRIPTION OF THE INVENTION

As was mentioned above, in attempting to blend organic polymers with inorganic compounds, the usual result is to obtain a phase separation. It has now been discovered that a useful substance may be obtained by means of the methods described herein. The resulting composition of matter is formed into a thin film membrane which may be utilized in gas detection systems. The utility of these membranes in gas detection devices is due to the fact that the membranes possess a high protonic conductivity, especially at room or ambient temperature, and are resistant to water.

Usually, a high conductivity is observed in polymer complexes only when the temperature is above the glass transition temperature (Tg), that is, above the temperature at which the substance changes from a glassy state to a rubbery state (the melting point of a polymer is usually above its glass transition temperature). Indications of the change of a polymer from a glassy state to a rubbery state are abrupt changes in certain properties, such as coefficient of expansion and heat capacity. The compositions of the present invention exhibit high protonic conductivity at temperatures well below the observed glass transition temperatures of the individual homopolymers. A device utilizing an ion-conducting polymer must operate below the Tg of the polymer; the polymer is not usable at higher temperatures due to loss of strength, tackiness, etc.

A distinct advantage which is possessed by the membranes of the present invention is that they possess relatively low resistivities (resistance times area divided by thickness). In using a gas sensor of the type of the present invention, it is necessary to measure the output voltage. When utilizing a membrane of the instant invention, it will be possible to use a voltage measuring device of relatively low impedance. Use of such a device will result in a simplified and lower cost electronics package for a commercial hydrogen sensor. A voltmeter should have an impedance (AC resistance) at least 3 orders of magnitude greater than that of the system in which it is used for measurement; high impedance voltage measuring devices are more costly than those of low impedance. In addition, a device with reduced impedance is less sensitive to electromagnetic interference than a high impedance device. This permits the device to be located in an electrically noisy environment without adversely affecting its performance.

The host polymer blend is a blend of an organic polymer and a phosphoric acid or sulfuric acid, the polymer being at least partially compatible with the acid. Examples of organic polymers which may be employed as one component of the host polymer blend of the present invention will include poly(vinyl alcohol), also known as PVA, polyethyleneimine, poly(acrylic acid), polyethylene oxide, phenol formaldehyde resins, poly(vinylpyrrolidone), poly(ethyloxazoline), poly(acrylamide), poly(vinylimidazole), poly(vinylpyridine), poly(vinyl sulfonic acid), etc. Further examples of organic polymers which may be employed include copolymers having monomer units of these exemplary polymers. In terms of monomer repeat units, the polymer-blend membrane comprises a polymer selected from a group of polymers or copolymers having repeat units selected from a group comprising hydroxyethylene, ethyleneimine, acrylic acid, ethylene oxide, 2-ethyl-2-oxazoline, acrylamide, N-substituted acrylamides, 4-vinylpyridine, methacrylic acid, N-vinylimidazole, vinyl sulfonic acid, 2-vinylpyridine, and polyphenolic structures such as phenol formaldehyde resins.

Examples of acids which may be employed in the host polymer blend will include hypophosphoric acid, metaphosphoric acid, orthophosphoric acid, pyrophosphoric acid, polyphosphoric acid, or sulfuric acid. The sulfuric acid which is employed will comprise an aqueous sulfonic acid which may contain from about 10% to about 40% sulfuric acid in aqueous solution. It is to be understood that the aforementioned organic polymers and phosphoric acids or sulfuric acid are only representative of the class of components which make up the membrane blends used in the present invention.

The guest polymer is formed from a monofunctional monomer selected from a group comprised of acrylic acid, methacrylic acid, acrylamide, methacrylamide, 2-acrylamido-2-methylpropanesulfonic acid, N-benzylacrylamide, N-ethylmethacrylamide, N-phenylacrylamide, and N-phenylmethacrylamide.

Examples of difunctional cross-linking agents for the guest polymer are methylenebisacrylamide, N,N-dialylacrylamide, m-xylenebisacrylamide, and N,N'-trimethylenebisacrylamide.

The host polymer blend used in the present invention is prepared by admixing the two components of the blend in a mutually miscible solvent at solution conditions for a period of time sufficient to form the desired blend. In the preferred host polymer blend the mutually miscible solvent which is employed to dissolve the components comprises water, although it is contemplated within the scope of this application that any other mutually miscible solvent, either inorganic or organic in nature may also be employed. The mixing of the two components of the host polymer may be effected at solution conditions which will include a temperature in the range of from about ambient (20°–25° C.) up to the boiling point of the mutually miscible solvent which, for example, in the case of water is 100° C. As an example, poly(vinyl alcohol) and orthophosphoric acid may be placed in a flask and dissolved in water which has been heated to 100° C.

The monofunctional monomer and cross-linking agent are then mixed with PVA and acid at a temperature ranging from ambient to about 50° C. The blend is cast upon a suitable casting surface which may consist of any suitable material sufficiently smooth in nature so as to provide a surface free of any defects which may cause imperfections on the surface of the membrane. Examples of suitable casting surfaces may include metals such as stainless steel, aluminum, etc., glass, polymer or ceramics. After casting the solution upon the surface, the solvent is then removed by any conventional means including natural evaporation or forced evaporation by the application of elevated temperatures whereby said solvent is evaporated and the desired membrane comprising a thin film is formed. Evaporation may be effected at room temperature over a period of time ranging up to about 24 hours may be effected by subjecting the film to elevated temperatures up to about 40° C. for a shorter time. Evaporation may also be effected by subjecting the solution to reduced pressure as low as 10 mm Hg at ambient or elevated temperatures. The thickness of the film can be controlled by the amount of phosphoric or sulfuric acid and/or polymer which is present in the reaction mixture or by the depth of the casting vessel. The thin film membrane which is prepared according to the process of the present invention will possess a thickness which may range from about 0.1 to over 500 microns and preferably from about 20 to about 100 microns.

After evaporation of the solvent, the resulting membrane is cured, or cross-linked, by various methods well known in the art. For example, the membrane may be subjected to radiation from an ultraviolet source or from an electron beam. Another method of curing, or polymerizing, the monomer is to subject the membrane to elevated temperatures ranging from about 50° to about 80° C. in an inert atmosphere, such as nitrogen, and in the presence of an activator, such as azoisobutyronitrile (AIBN). Curing is the final step in forming the membrane of this invention.

The amounts of phosphoric or sulfuric acid and organic polymer used in the host polymer blend may vary over a relatively wide range. For example, the acid may be present in the blend in a range of from about 16 mol% to about 50 mol% of the host polymer blend while the organic polymer may be present in an amount in the range of from about 84 mol% to about 50 mol% of the host polymer blend. Whenever a composition is expressed herein, it is to be understood that it is based, in the case of polymers, on the monomer repeat unit.

The mole ratio of monomer to cross-linking agent may vary from 35 moles of monomer to 1 mole of agent to 1 mole of monomer to 10 moles of agent. The mole ratio of host polymer blend to guest polymer may range from 5:1 to about 1:20.

It will be helpful in gaining an understanding of the invention to examine initial proof of principle experimentation. The information presented in regard to this experimentation is not meant to limit the scope of the invention in any way.

EXAMPLE 1

A solution was prepared by dissolving 0.5 gram of poly(vinyl alcohol) and 0.2 ml of 85% by weight orthophosphoric acid in boiling deionized water, the amount of water being sufficient to yield a total volume of 25 ml. The molecular weight of the PVA was 133,000. Other commercially available molecular weights could have been used. A second solution was prepared by mixing 2 grams of methylenebisacrylamide, 30.1 grams of methacrylic acid, and 25 grams of water. Portions of the two solutions in the amount of 6.7 ml and 10 ml respctively were mixed together and poured into a Petri dish, which served as a casting vessel. The water was allowed to evaporate for a period of 24 hours. The resulting film was transparent and possessed a thickness of 110 microns. The membrane was then irradiated by using an electron beam at a power of 175 kiloelectron volts (KEV) and a dose of 5 megarads (Mrad)/pass. It was irradiated on one side.

Figure 1:
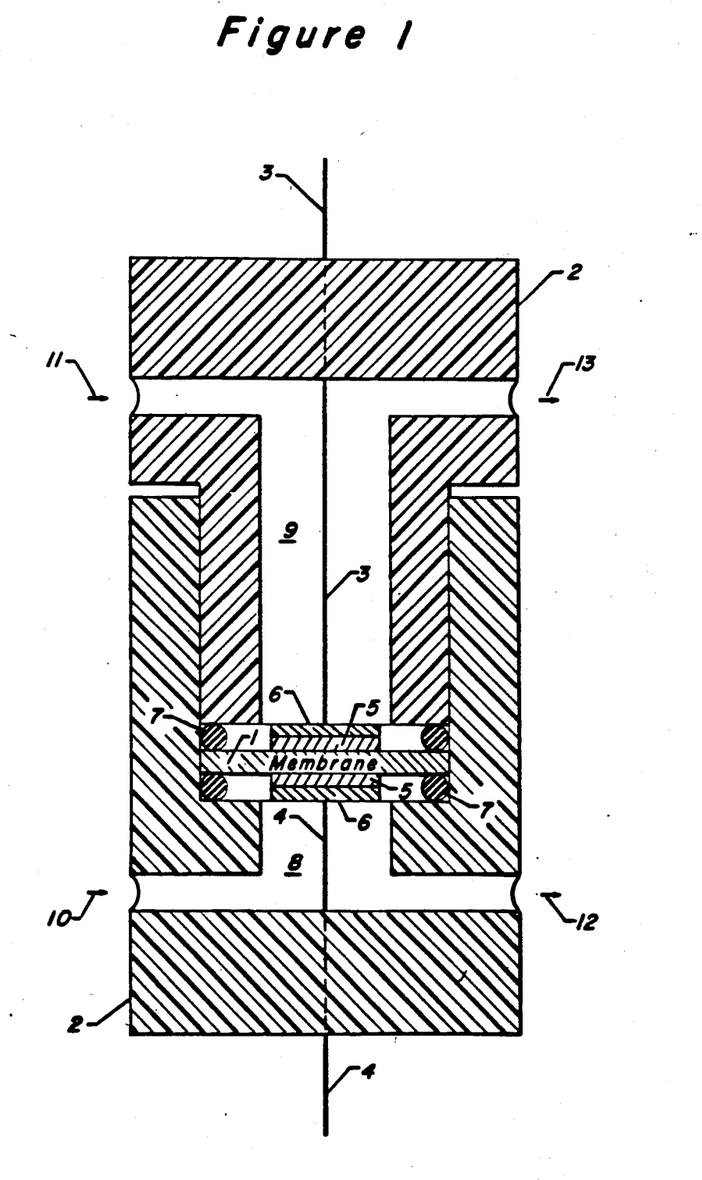
FIG. 1 is a schematic representation, in cross-section, of a test sensor used in initial proof of principle experimentation. The drawing is not to scale.

The thin film membrane was cut into a disc having a 1" diameter to form membrane 1 of FIG. 1 and platinum was sputter-deposited onto both sides of the disc. The deposited platinum discs each had a thickness of about 400 Angstroms and a diameter of about 1.4 cm. Deposition was accomplished by means of a Hummer II sputter deposition system supplied by Technics Co. A biased screen between the target and film was used to reduce the electron flux to the membrane. There are many alternative methods which could have been used to form the platinum deposits, such as thermal evaporation or deposition by means of an ink. The porous structure of sputter-deposited catalytic agent is helpful in facilitating spillover of hydrogen ions onto the membrane, but it is not required.

Referring to FIG. 1, membrane 1 was mounted in test fixture 2, which may also be referred to as a sample cell, membrane housing, or test sensor. The above mentioned platinum deposits 5 served as catalytic agent to promote dissociation and reassociation of hydrogen. Electrical contact was made to the platinum through copper platens 6, which were held in place by springs (not shown) extending etween the platens and interior surfaces of the sample cell. Platens 6 did not cover the entire surface of the catalytic agent, though FIG. 1 shows this to be the case. Note that when the catalytic agent is electrically conductive and not discontinuous, electrical contact need be made only at one point. Wire leads 3 and 4 extended from the platens out of the test fixture through means for sealing against gas leakage (not shown). Leads 3 and 4 were connected to EMF and current detecton means (not shown). Membrane 1 was sealed into test fixture 2 by O-rings 7 so that there were no gas leakage paths between test chamber 8 and reference gas chamber 9. Tubing (not shown) was connected at the gas inlets as denoted by arrows 10 and 11 to provide gas flow chambers 8 and 9 and was also connected to the gas outlets as denoted by arrows 12 and 13 to conduct gas away from the chambers. Gas cylinders and flow control apparatus (not shown) were used to provide gas to test the sensor of test fixutre 2 in accordance with the herein described experiments. Several cylinders of hydrogen/nitrogen gas mixtures were purchased; an analysis of the contents were supplied with each cylinder.

Gas flows were established through the chambers of the sample cell with both chamber pressures at about one atmosphere, since the chambers were vented directly to atmosphere. One flow was pure hydrogen (hydrogen partial pressure of approximately 1.0 atm.) and the other was alternated between pure hydrogen and about a 10% by volume mixture of hydrogen in nitrogen (hydrogen partial pressure of approximately 0.1 atm.). The voltage across wires 3 and 4 was recorded by means of a standard laboratory strip chart recorder. The voltage versus time plot was a substantially perfect square wave form. Voltage varied consistently between 0.1 millivolts and 29.2 mv. Response was Nernstian; the calculated voltage is approximately 29.1 mv (at a room temperature of about 22° C.). Note that this is open circuit voltage.

When an ammeter was connected to wires 3 and 4, the measured current was about $2 \times 10^{-3}$ ma. This corresponds to a current density of about $1.3 \times 10^{-3}$ ma/cm$^2$ and a hydrogen flux of $1.8 \times 10^{-5}$ ft$^3$/ft$^2$-hr; both figures being based on the area of the membrane covered by platinum. EMF across the membrane was measured when 100% hydrogen was flowing through both chambers of the sample cell. From this a resistivity of $2 \times 10^6$ ohm-cm was calculated. This applies to a totally dry membrane. When a membrane which had dried for only 1 hour, as mentioned above, was placed under test, the initial resistance was lower. The increase in resistance is due to removal of the water used in the casting process during initial operation of a sensor.

EXAMPLE 2

A sensor was prepared and tested in the same manner as that of EXAMPLE 1, except that both sides of the membrane were irradiated instead of one side as in EXAMPLE 1. The measured voltages were 0 mv and 29.0 mv. Resistivity was $6.9 \times 10^5$ ohm-cm. Hydrogen flux was $5 \times 10^{-5}$ ft$^3$/ft$^2$-hr.

EXAMPLES 3, 4 and 5

A sensor was prepared and tested in the same manner as that of EXAMPLE 1, except that the amounts of the components was varied as shown below. All amounts are in grams.

|  | Example 3 | Example 4 | Example 5 |
|---|---|---|---|
| PVA | 0.50 | 0.50 | 0.50 |
| orthophosphoric acid | 0.29 | 0.56 | 0.56 |
| methacrylic acid | 2.69 | 0.54 | 2.69 |
| methylenebisacrylamide | 0.18 | 0.04 | 0.18 |

The EMF difference (Delta EMF) in mv, resistivity in $10^5$ ohm-cm, and calculated hydrogen flux (F) in $ft^3/ft^2$-hr after at least 24 hours under test were as follows:

|  | Delta EMF | R | F |
|---|---|---|---|
| Example 3 | 28.9 | 51 | $6.2 \times 10^{-6}$ |
| Example 4 | 29.3 | 1.9 | $1.9 \times 10^{-4}$ |
| Example 5 | 29.4 | 2.3 | $1.3 \times 10^{-4}$ |

Water solubility was tested by placing membranes made in accordance with the above examples in boiling water. Also placed in boiling water was a membrane cast from a solution of PVA and orthophosphoric acid in a 3.8 to 1 mole ratio (Example 6). The two component membrane dissolved in about 90 seconds while the interpenetrating polymer network membranes were unaffected after 15 minutes in boiling water.

In addition to platinum, palladium may be deposited on membranes for use as catalytic agent. Other catalytic agents are available and known to those skilled in the art. The catalytic agent need not be electrically conductive; however, then the means for forming electrical connection must be in contact with the catalytic agent over a broad area, to faciliate movement of electrons from sites of the catalytic agent to the electrically conductive substance, or electrode. Areas of membrane which are not adjacent to catalytic agent are not effective in the invention. Hydrogen ions spill over from the catalytic agent to the membrane and then the protons move through the membrane.

Sensors utilizing the present membrane have not yet been tested with sample gases containing small amounts of potential poisons. However, it is believed that the present membranes will exhibit the same behavior as certain other membranes which were tested, since interference occurs mainly at the electrodes. In these tests, addition of carbon monoxide in an amount of about 0.1% by volume in a hydrogen sample gas stream with a 100% hydrogen reference gas stream caused a change in EMF indicative of a large reduction in hydrogen partial pressure. This apparent drop in hydrogen concentration was much larger than the expected drop due to the effect of dilution of sample gas with CO. This is likely due to the competition by CO with molecular hydrogen for adsorption sites on platinum. No interference with the hydrogen concentration measurements was detectable when 100 PPM by volume of CO was added to a sample gas stream. It is expected that the present invention cannot be used to measure the amount of hydrogen, or other gas, present in a sample gas which also contains significant amounts of CO, or other substances which interfere in the same manner, unless the amount of CO, or other substance, is known by other means or constant. The following potential poisons did not interfere with hydrogen concentration measurements made using the other membranes: hydrogen chloride (10 PPM), hydrogen sulfide (3%), carbon dioxide (100 PPM), methane (3%), and butane (3%). All of the concentrations in sample gas shown in parenthesis are by volume.

It is believed that membranes of the present invention will operate at temperatures ranging from minus 30° C. to plus 50° C. and will exhibit Nernstian behavior, though, of course, the voltage varies with temperature. It may be possible to use these membranes at higher temperatures, but no tests have been conducted.

The above description of the invention has dealt with hydrogen detection. It is clear that any substance capable of dissociating in the presence of a catalyst to yield hydrogen ions may be detected in the same manner. An example is hydrogen chloride (using palladium or nickel catalyst if HCl is at room temperature). The Nernst equation applies a manner similar to that described herein. The invention is also useful in detecting any gaseous component of a gas sample which is capable of combining with hydrogen ions. Oxygen may be used to illustrate this embodiment. Protons passing through the membrane from a reference gas chamber containing pure hydrogen will combine with oxygen in a sample gas and electrons from the external circuit (for example, wires 3 and 4 of FIG. 1) to form water, in contrast to a hydrogen detector, wherein hydrogen is formed. The Nernst equation is applicable; the $E_o$ term is not 0, as it is when the same substance is present on both sides of the membrane, and the partial pressure of oxygen to the one-half power times the partial pressure of hydrogen divided into the partial pressure of water replaces the analogous term of the equation. Hydrocarbons capable of hydrogenation or dehydrogenation may be subjects of detection. Examples are cyclopentadiene, benzene, isoprene, cyclohexane, and isoamylene.

It is often desirable to avoid the use of a reference gas in the methods and apparatus of detection described herein. This may be accomplished by using a reference substance in the form of a solid. As discussed herein, it is necessary that a substance with a known partial pressure of hydrogen be used as a reference. It is also necessary that the reference partial pressure remains substantially constant as hydrogen is added to or removed from the reference substance.

Figure 3:
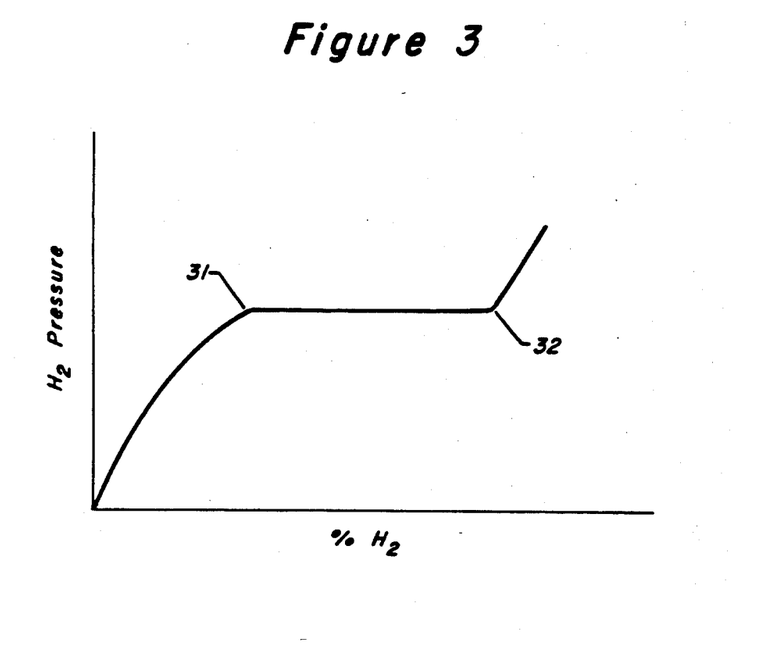
FIG. 3 is a portion of a phase diagram of a solid reference substance capable of use in an embodiment of the present invention, in which hydrogen partial pressure of the substance is plotted against the amount of hydrogen in the substance. If the plot were extended to larger amounts of hydrogen, several plateaus might appear.

In the sensor of the present invention, the EMF developed is an open circuit value. Thus, theoretically there are no electrons flowing in the external circuit to combine with protons passing through the membrane and therefore no change in reference hydrogen concentration. Of course, in actuality there is a small current flowing and reference hydrogen concentration is constantly changing. A reference substance must possess the characteristic of constant hydrogen partial pressure while hydrogen concentration changes. FIG. 3 depicts a portion of a phase diagram of a solid substance suitable for use as a reference substance in the present invention. For a sensor having a solid reference substance to function properly, the hydrogen concentration must lie in the plateau, or horizontal portion, of the curve of FIG. 3, the plateau lying between points 31 and 32. As the hydrogen content of the reference substance increases or decreases due to operation of the sensor, that is, as hydrogen, or other substance, forms from the protons which pass through the membrane and the electrons which flow in the external circuit, the point representing the reference substance moves along the plateau. However, as long as the point is on the plateau the hydrogen partial pressure remains constant and, therefore, the reference substance is useful. It can be seen that a particular reference substance has a limited life.

Since the time required to change the hydrogen concentration beyond the limits represented by points 31 and 32 can easily be measured in months or years, the use of a solid reference is practical. Since the flow of protons through the membrane may be in either direction, hydrogen content of the solid reference substance may increase or decrease. When it passes above point 32 or below point 31, the reference substance must be replaced.

Metal hydrides are, in general, suitable for use as solid reference substances in this invention, since their phase diagrams are usually similar to that of FIG. 3. There may be several plateaus on one diagram, so that there is a choice of reference partial pressures while using one particular substance. Examples of metal hydrides include substances consisting of hydrogen and oxygen with tungsten, molybdenum, vanadium, or iridium, hydrogen-zirconium-nickel compounds, hydrogen-zirconium-platinum compounds, and compounds of hydrogen with platinum, palladium, zirconium, hafnium and/or vanadium. Further examples comprise compounds of hydrogen and elements of atomic numbers 3, 11, 12, 19 through 28, 37 through 48, 55 through 60, 62, 64, 72 through 78, 90, and 92.

The present membranes have not been tested with a solid reference substance. However, it is expected that the present membranes will exhibit the same behavior as certain other membranes which were tested in the following manner. In proof of principle experimentation, the apparatus of FIG. 2 was fabricated. Palladium layer 42 of approximately 5000 angstroms thickness was sputter-deposited on substrate 41. The substrate used was alumina. Choices of substrate may be made from a wide variety of materials and are not a part of the invention. The palladium layer was moistened with DI water and a 63/37 PVA/H$_3$PO$_4$ membrane 43 was cast over it in the same manner as described above. The membrane had a thickness of approximately 40 microns. Platinum layer 44 was sputter-deposited on membrane 43 to a thickness of approximately 400 angstroms. Wires 45 and 46 were attached to platinum layer 44 and palladium layer 42. The wires were connected to voltmeter 47. In addition, switch 48 was provided in parallel with the voltmeter to complete an external circuit when desired.

Figure 2:
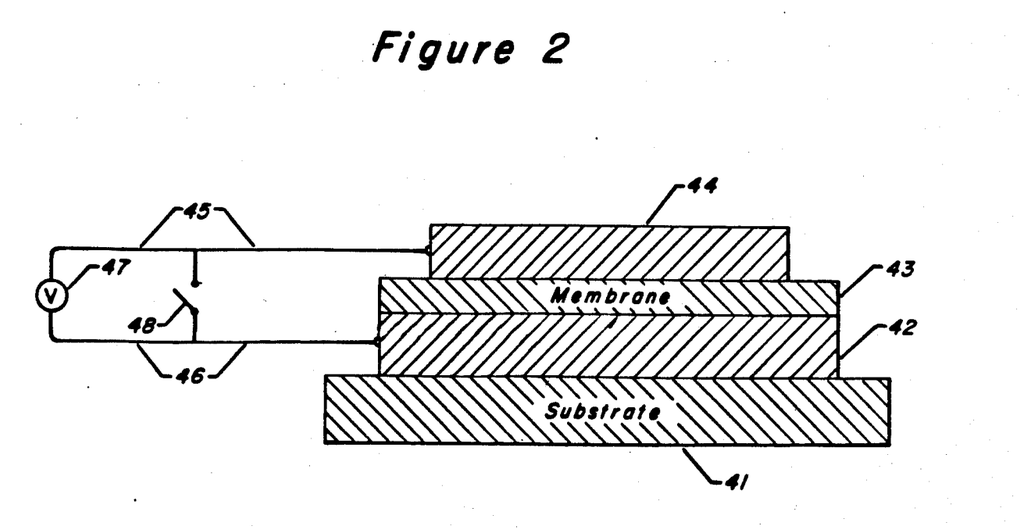
FIG. 2 is a schematic representation, in cross-section, of a test sensor which may be used in experimentation for the embodiment which utilizes a solid reference substance. It is not to scale.

The apparatus was exposed to hydrogen gas for about two hours, with switch 48 closed, to add hydrogen to palladium layer 42 to provide the reference substance. Hydrogen dissociated at platinum layer 44 and the protons passed through membrane 43 while the electrons from the dissociated molecules flowed through the external circuit consisting of wires 45 and 46 and switch 48. It is not necessary to form the reference substance in place in this manner; palladium hydride could have been deposited on the substrate. The palladium hydride served as both catalytic agent and reference substance.

The apparatus depicted in FIG. 2 is an example of a sample cell or membrane housing. The space adjacent to catalytic agent 44 comprises the sample gas chamber. The space occupied by reference substance 42 comprises the reference chamber. Membrane 43 comprises a substantially imporous partition separating the chambers. If it were desired to use a catalytic agent separate from the reference substance, catalytic agent would be depicted as a layer between the layers 42 and 43.

After completion of fabrication of the sensor, it was placed in a closed chamber and pure hydrogen gas was passed over the sensor. Switch 48 was open, since it is used only during fabrication of the sensor, i.e., during hydrogenation of the palladium. A valve in the outlet tubing from the closed chamber was partially closed to throttle hydrogen flow out of the chamber and increase chamber pressure. Voltage at various pressures were recorded and found to match values calculated using the Nernst equation.

The reference partial pressure of hydrogen which is used in the Nernst equation to determine EMF is easily calculated. For example, niobium hydride has a hydrogen partial pressure of approximately $10^{-6}$ atmospheres, as calculated by the relationship below. Note that in the plateau region of the phase diagram, niobium hydride and certain other hydrides exist in three phases, two condensed and one gaseous (molecular hydrogen).

$$\tfrac{1}{2}\ln P = \frac{A}{RT} - \frac{B}{R},$$

where A = enthalpy difference between the two hydride phases expressed in kcal/gm-atom, B = entropy difference between the two hydride phases expressed in cal/gm-atom-°K., P = P$_2$ or P$_1$ as defined above, and R and T are as defined above.

Figure 4:
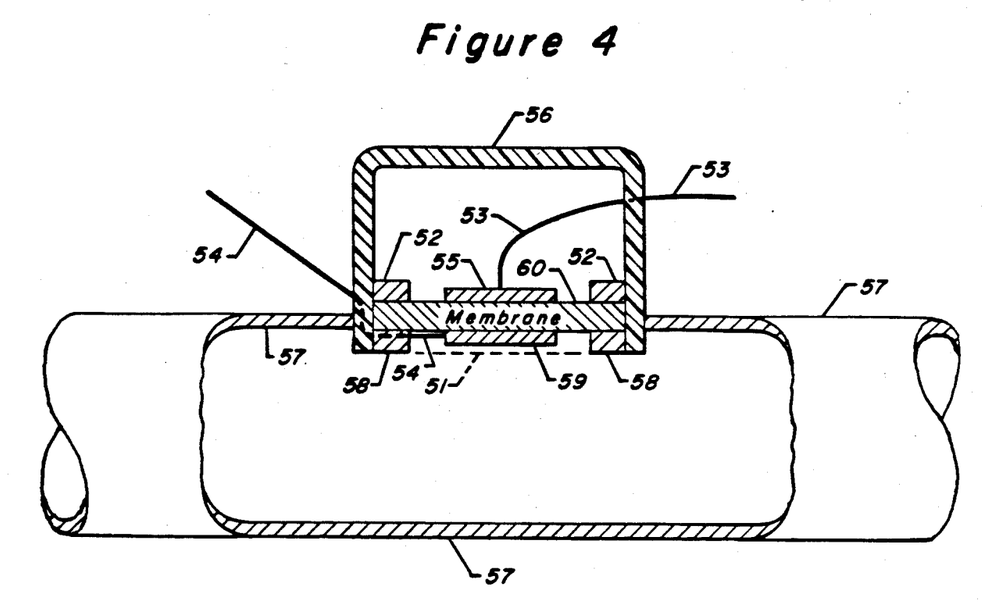
FIG. 4 depicts, in a sectional view, a sensor with a sealed reference chamber mounted in a pipeline. It is not to scale and has non-essential elements omitted.

It can be seen that a membrane mounted in a cell such as depicted in FIGS. 1 and 4 may be subjected to high differential pressures which may deform or burst the membrane. A composite membrane or supported membrane assembly may be used when a high differential pressure across the membrane is expected. A composite membrane may be fabricated by casting a solution prepared as described above on a flexible porous support and then curing it. A supported membrane assembly may be fabricated by attaching a membrane which is cast, dried, and cured as above to a rigid porous support. A supported membrane may also be fabricated by impregnating a rigid porous support with solid electrolyte, allowing it to dry, casting a membrane on the support and allowing it to dry, and then casting another membrane on the reverse side, thus forming a continuous solid electrolyte path from the outer surface of the membrane on one side through the electrolyte to the outer surface of the membrane on the other side of the support. It is contemplated that any porous substrate which possesses a structural strength greater than the thin film membrane may be employed. Some examples of these porous supports will include substances such as glass cloth, polysulfone, cellulose acetate, polyamides, ceramics such as alumina, glass, procelain, etc. which have been fabricated to possess the necessary porosity, etc. The amount of blend which is cast upon the flexible porous support will be that which is sufficient to form a thin film membrane having a thickness within the range herein set forth.

Composite membranes using the composition of matter of the present invention have not been tested, though supported membranes of the present invention have been tested. However, it is expected that present composited membranes will exhibit behavior at least as good as the tested composited membranes. In one test, a polymer blend was prepared by dissolving 0.5 gram of 16,000 molecular weight poly(vinyl alcohol) and 0.2 ml of orthophosphoric acid in boiling deionized water, the amount of organic polymer and acid being sufficient to impart a 63/37 wt.% ratio to the resulting polymer blend. After a period of time sufficient to form the blend had passed, the solution was stirred and poured onto the top of a fine glass cloth which was positioned in a standard Petri dish. The water was allowed to evaporate for a period of 48 hours and the resulting membrane composite comprising a thin film membrane composited on, or with, the glass cloth having a thickness of 95 microns was recovered.

The PVA/H$_3$PO$_4$ composite membrane was cut into a circle having a 1" diameter and platinum electrodes were sputter-deposited on each side of the membrane. The membrane was then placed in a sample housing similar to that of FIG. 1. A reference gas consisting of 100% hydrogen and a sample gas comprising 90.013% nitrogen and 9.987% hydrogen were each passed through the two chambers. An EMF of 29.6 mv was measured; this compares to a calculated voltage of 29.5 millivolts at a temperature of 25.3° C. In addition, it was found that the resistivity was 0.375×10$^5$ ohm-cm.

As an illustration of the greater structural strength of a polymer blend on a porous flexible support when compared to unsupported membranes reference may be made to previous experiments. In previous experiments, two polymer blend membranes were prepared. The polymer blend was prepared by dissolving 0.5 gram of poly(vinyl alcohol) having a molecular weight of 16,000 and 0.2 ml of orthophosphoric acid in boiling deionized water. The resulting blend was cast onto a glass cloth having a thickness of 30 microns. A second blend was prepared by admixing like proportions of poly(vinyl alcohol) and orthophosphoric acid and casting the resulting blend onto a Petri dish without a support. After removal of the solvent, the two membranes were recovered.

Each membrane was placed in a holder which enabled air pressure to be exerted against one side of the membrane while the other side was at atmospheric pressure. When exposed to 5 psig, the unsupported membrane burst at its center in less than 1 minute. At 2 psig another sample of unsupported membrane bulged and was permanently deformed. The composite membrane was subjected to various pressure levels in 5 psig increments with one minute hold time between increases in pressure. It burst at 35 psig, shearing at the edges of the test hole in the holder. The point of failure leads one to believe that holder design caused the shearing and that a higher burst pressure would be observed in a different holder.

In an experiment using the composition of matter of the present invention, a supported hydrogen sensor was made by impregnating a porous ceramic support with a water solution containing 2 grams PVA, 2.2 grams orthophosphoric acid, 5.39 grams methacrylic acid, 0.36 grams methylenebisacrylamide, and 0.06 grams AIBN. A Coors porous ceramic substrate measuring 1½ inch diameter and 1/8 inch thick was soaked in the solution and allowed to dry. Additional solution was applied to each side of the impregnated substrate and allowed to dry. The sensor was heated in nitrogen for 2 hours at 75° C. The formation of the interpenetrating polymer network was confirmed after two hours by placing a film of the above composition made at the same time in boiling water for 15 minutes. The film did not dissolve. Platinum electrodes were sputter-deposited on each side of the sensor as described previously. The sensor detects hydrogen and has a total device resistance in 100% hydrogen of 1.07 megohm. When a differential of 100 psig was established across this supported sensor, there was no damage to the sensor.

The membranes of the present invention are quite strong and durable, as can be seen from values obtained for the bulk modules. The membrane of Example 6 consisted of a blend of PVA and phosphoric acid in a 3.8:1 mole ratio. Examples 3 and 5 were interpenetrating polymer networks where the host polymer blend was PVA and orthophosphoric acid in 3.8:1 and 2:1 mole ratios, respectively. In the following table, the bulk modulus was measured at 25° and 50° C. and is expressed in meganewtons per square meter.

|           | Modulus @ 25 | Modulus @ 50 |
|-----------|--------------|--------------|
| Example 6 | 85           | 65           |
| Example 3 | 1093         | 503          |
| Example 5 | 237          | 217          |

As is common in many analysis instruments, the sample gas provided to a sensor may require conditioning in order to achieve effective detection. Of course, any particulate matter and liquid droplets are removed. The extent of conditioning depends on the particular gas involved and its state. For example, an extremely hot gas must be cooled to a sufficiently low temperature so as not to degrade the apparatus by melting sensor components, including the membrane. A relatively cold gas may need to be heated to a temperature which promotes a reasonable response time of the apparatus. A related factor to be considered is the necessity for knowing the temperature for use in the Nernst equation. The temperature may be measured or the temperature may be maintained at a pre-established constant value. If the calibration gas temperature is maintained at the same value, the matter is simplified. Water vapor and/or other substances are often removed from or added to a sample gas stream. However, removal of water in the practice of the present invention is not necessary, since the membrane is stable in the presence of water (as discussed above). Other sample-conditioning techniques may be required. For example, in a situation where the concentration of the unknown substance is extremely large and capable of saturating the apparatus, the sample may be diluted by addition of a known amount of inert gas. The actual concentration of undiluted sample can then easily be calculated.

A detector may take many forms. A portable battery-operated unit may be used as a "sniffer" to detect the presence in the atmosphere of a particular gas due to leakage from a closed system. A detector may be permanently mounted in a particular location to detect leaks. When conditioning is not required, a detector may be fabricated for insertion directly into a process pipeline. When a gas sample must be conditioned, a small sidestream may be withdrawn from a process pipeline on a continuous or intermittent basis and passed through a sample gas chamber. A quantity of reference gas may be sealed into a reference gas chamber instead of providing a continuous flow.

Figure 5:
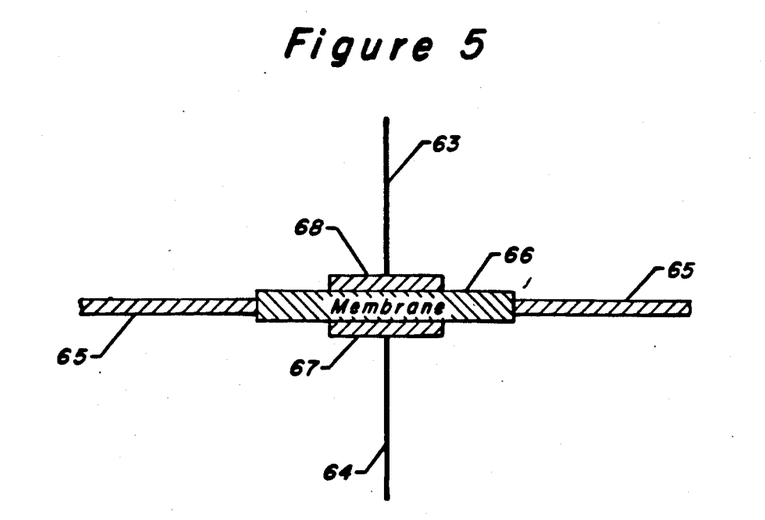
FIG. 5 depicts an embodiment of the invention, in a sectional view, in which a membrane is part of a partition separating a sample gas chamber from a reference chamber.

As used herein, the term "detection" includes not ionly sensing presence or absence of the detected substance, but measurement of the amount of substance present, either in order of magnitude or exact amounts. Gas sample refers to any portion of a gas which is the subject of detection. A gas sample may have only one component. Sample cell or membrane housing or test fixture refers to a housing or fixture which holds an electrolyte element and other required components. FIG. 5 depicts a membrane housing. Sensor is a general term denoting sensing apparatus, such apparatus comprising a membrane housing. Membrane or electrolyte element refers to an ion-conducting substance suitable for use as an electrolyte in the concentration cell of this invention which has been formed into a particular physical entity, either with or without additional substances, for use in the invention. Where an electrolyte element surface is referred to as in common with a gas or gas chamber, the meaning is the same as exposed to a gas or gas chamber and such reference does not preclude the presence of a catalytic agent and electrodes at or covering the surface. Gas may diffuse through covering material. Sample gas chamber refers to any space in which gas which is the subject of detection exists. For example, a sample cell can form a part of a pipeline wall such that the gas flowing in the pipeline is the sample gas and the pipeline is the sample gas chamber. The term "gas" is used herein to include vaporized liquids regardless of boiling point characteristics of the substance. As used herein, miscible means capable of being mixed where there may only be a very small degree of solubility. As is familiar to those skilled in the art, the terms concentration and partial pressure are often used interchangeably; partial pressure expresses concentration. Compatible may be taken to mean that compatible compounds will form the polymer-blend composition of matter.

The design of sample cells, or detectors, or membrane housings, is well known. Many configurations are possible; FIG. 1 provides an example of one type. FIG. 4 depicts an embodiment of the invention where membrane housing 56 is mounted (attachment means not shown) in the wall of pipeline 57. Gas is present and may or may not be flowing in the pipeline. The sample gas chamber is the interior of the pipe adjacent to housing 56, while the reference chamber is defined by housing 56 and solid electrolyte membrane 60. Reference gas is sealed into the reference gas chamber; thus it is necessary to replace the reference gas at intervals upon its changing in concentration as a result of the cell reaction sufficiently to affect sensor results. It should also be noted that the membrane is not expected to be totally impermeable and that substances in addition to hydrogen ion may pass through it. Permeability experimentation has not been accomplished, except to the extent indicated herein. Alternatively, the reference chamber may contain a solid reference substance. Electrically conductive catalytic agent is present on both sides of membrane 60, as shown by reference numbers 55 and 59. Wire leads 53 and 54 extend outside the apparatus for connection to voltage detection means. Retaining rings 52 and 58 serve to hold membrane 60 in place at its perimeter (exact detail not shown). Screen 51 is provided to protect membrane 60 from the impact of large particles or objects. If a greater membrane surface area than that of FIG. 4 is desired, a detector may be fabricated in the form of a cylindrical probe for insertion into a pipeline. Membrane material may be placed over a perforated pipe which is sealed at one end. The interior of the perforated pipe is the reference gas chamber. It may be desirable to protect the membrane and catalytic agent by covering it with a porous substance through which sample gas can pass.

Referring to FIG. 5, an embodiment of the invention in which a membrane 66 serves as a part of a partition 65 is shown. Partition 65 separates a sample gas chamber from a reference gas chamber. Catalytic agent 67 and 68 and wire leads 63 and 64 perform the functions discussed above.

We claim as our invention:

1. Apparatus for detection, in a gas sample, of a gaseous component which is capable, in the presence of a catalytic agent, of dissociating to yield hydrogen ions or of combining with hydrogen ions comprising:
   (a) an interpenetrating polymer network membrane which comprises a host polymer blend and a guest polymer, wherein the host polymer blend is comprised of (1) an acid selected from the group consisting of phosphoric acids and sulfuric acid and (2) a component selected from the group consisting of (i) a polymer selected from the group consisting of poly(hydroxyethylene), poly(ethyleneimine), poly(acrylic acid), poly(ethylene oxide), poly(2-ethyl-2-oxazoline), phenol formaldehyde resins, poly(acrylamide), poly(N-substituted acrylamide), poly(4-vinylpyridine), poly(methacrylic acid), poly(N-vinylimidazole), poly(vinyl sulfonic acid), and poly(2-vinylpyridine) and (ii) copolymers having monomer units of (i); and wherein the guest polymer is comprised of (1) a monofunctional monomer selected from the group consisting of acrylic acid, methacrylic acid, acrylamide, methacrylamide, 2-acrylamido-2-methylpropanesulfonic acid, N-benzylacrylamide, N-ethylmethacrylamide, N-phenylacrylamide and N-phenylmethacrylamide and (2) a difunctional cross-linking agent selected from the group consisting of methylenebisacrylamide, N,N-diallylacrylamide, m-xylenebisacrylamide and N,N'-trimethylenebisacrylamide, with the proviso that the monofunctional monomer which is employed to form the guest polymer differs from any of the monomeric repeat units which comprise the organic polymer in the host polymer blend;
   (b) a membrane housing comprising a sample gas chamber and a reference substance chamber separated by a partition comprising said membrane, said membrane having a first surface in common with the sample gas chamber and a second surface in common with the reference substance chamber;
   (c) two separate portions of catalytic agent effective to promote dissociation and combination, a first portion in contact with said first surface and a second portion in contact with said second surface of said membrane;
   (d) means for forming electrical connection in operative contact with said catalytic agent at said first surface and with said catalytic agent at said second surface;
   (e) means for measuring EMF between said first and second surfaces;
   (f) means to supply sample gas to said sample gas chamber; and
   (g) means to provide an indication of the presence of hydrogen or of a gas capable of combining with hydrogen ions based on the measured EMF.

2. The apparatus of claim 1 further characterized in that said catalytic agent is electrically conductive.

3. The apparatus of claim 1 further characterized in that said catalytic agent is porous to said gaseous component.

4. The apparatus of claim 1 further comprising means to supply reference gas to said reference substance chamber.

5. The apparatus of claim 1 further including means to convert said EMF to concentration.

6. The apparatus as set forth in claim 1 in which said phosphoric acid is present in said host polymer blend in an amount in the range of from about 16 mol% to about 50 mol% and said polymer is present in said host polymer blend from about 50 mol% to about 84 mol%.

7. The apparatus as set forth in claim 1 in which said monofunctional monomer and said difunctional cross-linking agent are present in quantities such that the mole ratio of said monomer to said cross-linking agent varies from about 35:1 to 1:10.

8. The apparatus as set forth in claim 1 in which said membrane possesses a thickness of from about 0.1 to about 500 microns.

9. The apparatus as set forth in claim 1 in which the mole ratio of said host polymer blend to said guest polymer is from about 5:1 to about 1:20.

10. The apparatus as set forth in claim 1 in which said host polymer blend comprises poly(vinyl alcohol) and orthophosphoric acid.

11. The apparatus of claim 1 further characterized in that said monofunctional monomer is methacrylic acid and said cross-linking agent is methylenebisacrylamide.

12. The apparatus as set forth in claim 1 in which said interpenetrating polymer network is composited with a flexible porous support comprising glass cloth.

13. The apparatus as set forth in claim 1 in which said interpenetrating polymer network is utilized with a rigid porous support.

14. The apparatus of claim 1 further characterized in that said reference substance chamber contains a reference gas.

15. The apparatus of claim 1 further characterized in that said reference substance chamber contains a reference substance in solid form, which reference substance is in contact with said second portion of catalytic agent and exhibits a substantially constant known hydrogen partial pressure.

16. The apparatus of claim 15 further characterized in that said reference substance is a metal hydride.

17. The apparatus of claim 16 further characterized in that a single substance serves as both reference substance and catalytic agent.

18. The apparatus of claim 17 further characterized in that said reference substance and catalytic agent is palladium hydride.

19. A method for detection, in a gas sample, of a gaseous component which is capable, in the presence of a catalytic agent, of dissociating to yield hydrogen ions or of combining with hydrogen ions, such method comprising contacting said gas sample with a first surface of an interpenetrating polymer network membrane and detecting EMF between means for forming electrical connection with two separate portions of a catalytic agent effective to promote dissociation and combination, where a first portion of catalytic agent is in contact with said first surface of said membrane and a second portion of catalytic agent is in contact with a second surface of said membrane, which membrane isolates said gas sample from a reference substance and has said second surface exposed to the reference substance, said membrane comprising a host polymer blend and a guest polymer, wherein the host polymer blend is comprised of (1) an acid selected from the group consisting of phosphoric acids and sulfuric acid and (2) a component selected from the group consisting of (i) a polymer selected from the group consisting of poly(hydroxyethylene), poly(ethyleneimine), poly(acrylic acid), poly(ethylene oxide), poly(2-ethyl-2-oxazoline), phenol formaldehyde resins, poly(acrylamide), poly(N-substituted acrylamide), poly(4-vinylpryridine), poly(methacrylic acid), poly(N-vinylimidazole), poly(vinyl sulfonic acid), and poly(2-vinylpyridine) and (ii) copolymers having monomer units of (i); and wherein the guest polymer is comprised of (1) a monofunctional monomer selected from the group consisting of acrylic acid, methacrylic acid, acrylamide, methacrylamide, 2-acrylamido-2-methylpropanesulfonic acid, N-benzylacrylamide, N-ethylmethacrylamide, N-phenylacrylamide and N-phenyllmethacrylamide and (2) a difunctional cross-linking agent selected from the group consisting of methylenebisacrylamide, N,N-diallylacrylamide m-xylenebisacrylamide and N,N'-trimethylenebisacrylamide, with the proviso that the monofunctional monomer which is employed to form the guest polymer differs from any of the monomeric repeat units which comprise the organic polymer in the host polymer blend.

20. The method of claim 19 further characterized in that said gaseous component is elemental hydrogen.

21. The method of claim 19 further characterized in that said gaseous component is elemental oxygen.

* * * * *